(12) United States Patent
Stoop et al.

(10) Patent No.: US 9,636,095 B2
(45) Date of Patent: May 2, 2017

(54) OCCLUDER (75) Inventors: Hans Stoop, Diepflingen (CH); Mischa Häfelfinger, Gelterkinden (CH)

(73) Assignee: CARAG AG, Baar (CH)

( * ) Notice: Subject to any disclaimer, the term of this patent is extended or adjusted under 35 U.S.C. 154(b) by 497 days.

(21) Appl. No.: 13/383,357

(22) PCT Filed: Jun. 15, 2010

(86) PCT No.: PCT/CH2010/000155
§ 371 (c)(1),
(2), (4) Date: Mar. 27, 2012

(87) PCT Pub. No.: WO2011/003213
PCT Pub. Date: Jan. 13, 2011

(65) Prior Publication Data
US 2012/0179190 A1    Jul. 12, 2012

(30) Foreign Application Priority Data

Jul. 10, 2009  (CH) ..................................... 1073/09
Jan. 22, 2010  (CH) ..................................... 0086/10

(51) Int. Cl.
A61B 17/00         (2006.01)
(52) U.S. Cl.
CPC  *A61B 17/0057* (2013.01); *A61B 2017/00575* (2013.01); *A61B 2017/00592* (2013.01);
(Continued)
(58) Field of Classification Search
CPC ...... A61B 17/0057; A61B 2017/00575; A61B 2017/00862; A61B 2017/00606;
(Continued)

(56) References Cited

U.S. PATENT DOCUMENTS 5,725,552 A * 3/1998 Kotula et al. ................. 606/213
5,861,003 A * 1/1999 Latson et al. ................. 606/213
(Continued)

FOREIGN PATENT DOCUMENTS

WO    01/49185    7/2001
WO    03/061481   7/2003
(Continued)

OTHER PUBLICATIONS

International Search Report for International App. No. PCT/CH2010/000155, completed Sep. 15, 2010.

*Primary Examiner* — Christopher L Templeton
*Assistant Examiner* — Lucas Paez
(74) *Attorney, Agent, or Firm* — McDonnell Boehnen Hulbert & Berghoff LLP (57) ABSTRACT An occluder for closing an opening in a circuit system can be transferred from a compact manifestation which extends along a longitudinal axis into an expanded manifestation. The occluder has a first expansion unit and a second expansion unit which bear on in each case one side of the opening in the expanded manifestation. Furthermore, the occluder has a first coupling part and a second coupling part which can be brought into engagement with one another, with the result that they fix the occluder in its expanded manifestation. The first coupling part has a region which extends between the first and second expansion units in the expanded manifestation. According to the invention, this region is configured such that it can expand along the longitudinal axis. It is preferably configured such that it can expand counter to a restoring force, that is to say resiliently or elastically. This occluder therefore permits automatic setting of the spacing between two expansion and/or closure units according to the structural conditions at the location of the opening to be closed.

14 Claims, 7 Drawing Sheets

(52) U.S. Cl.
CPC ............... *A61B 2017/00606* (2013.01); *A61B 2017/00619* (2013.01); *A61B 2017/00862* (2013.01)

(58) Field of Classification Search
CPC A61B 2017/00619; A61B 2017/00592; A61B 2017/00588; A61B 2017/00597
USPC .................................. 606/151, 191, 213, 215
See application file for complete search history.

(56) References Cited

U.S. PATENT DOCUMENTS

| | | | | |
|---|---|---|---|---|
| 7,087,072 | B2* | 8/2006 | Marino et al. | 606/213 |
| 7,691,115 | B2* | 4/2010 | Corcoran et al. | 606/157 |
| 8,257,389 | B2* | 9/2012 | Chanduszko | A61B 17/0057 |
| | | | | 606/213 |
| 8,313,505 | B2* | 11/2012 | Amplatz et al. | 606/200 |
| 8,551,135 | B2* | 10/2013 | Kladakis | A61B 17/0057 |
| | | | | 606/139 |
| 8,715,319 | B2* | 5/2014 | Cahill | 606/215 |
| 8,764,790 | B2* | 7/2014 | Thommen et al. | 606/213 |
| 8,870,913 | B2* | 10/2014 | Opolski | A61B 17/0057 |
| | | | | 606/151 |
| 2004/0176799 | A1* | 9/2004 | Chanduszko et al. | 606/213 |
| 2005/0065547 | A1* | 3/2005 | Marino | A61B 17/0057 |
| | | | | 606/213 |
| 2007/0129755 | A1 | 6/2007 | Abbott et al. | |
| 2007/0179527 | A1* | 8/2007 | Eskuri et al. | 606/213 |
| 2008/0065148 | A1* | 3/2008 | Corcoran et al. | 606/213 |
| 2008/0249562 | A1 | 10/2008 | Cahill | |

FOREIGN PATENT DOCUMENTS

| | | |
|---|---|---|
| WO | 2005/074813 | 8/2005 |
| WO | 2005/110240 | 11/2005 |
| WO | 2006/041612 | 4/2006 |
| WO | 2007/115109 | 10/2007 |
| WO | 2007/115117 | 10/2007 |

* cited by examiner

OCCLUDER

CROSS REFERENCE TO RELATED APPLICATIONS

The present application is a U.S. National Phase Application pursuant to 35 U.S.C. §371 of International Application No. PCT/CH2010/000155 filed Jun. 15, 2010, which claims priority to Swiss Patent Application No. 1073/09 filed on Jul. 10, 2009 and Swiss Patent Application No. 86/10 filed on Jan. 22, 2010. The entire disclosure contents of these applications are herewith incorporated by reference into the present application.

TECHNICAL FIELD

The present invention relates to an occluder.

BACKGROUND

Occluders are implants that are used for occluding passages or openings in circulatory systems, such as blood vessels or shunt connections, and are usually positioned and expanded via a sheath introduced into a vein. Occluders serve in particular for occluding openings in the heart or in another bodily channel in the human or animal body. By way of example, occluders serve to occlude a patent ductus arteriosus (PDA), an atrial septal defect (ASD) or a ventricular septal defect (VSD). Other applications in the human and animal body are possible.

The prior art has disclosed the most diverse types of embodiments for occluders. By way of example, occluders can be embodied as a helical spring or can be opened like an umbrella. Furthermore, they can occlude the passage from only one side or from both sides. These occluders can usually be brought into an elongate form so that by means of the catheter they can be brought to the passage that should be occluded. There the occluder is released and it assumes the expanded usage form thereof, either independently or in a guided fashion.

Figure 1:
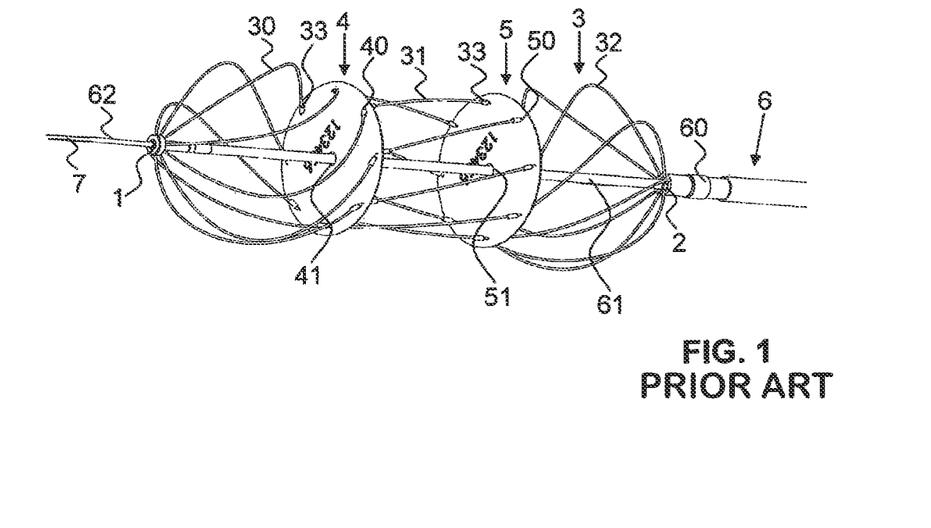
FIG. 1 shows an occluder as per the prior art in a manifestation that illustrates the transition between a compact and an expanded manifestation.
Figure 2:
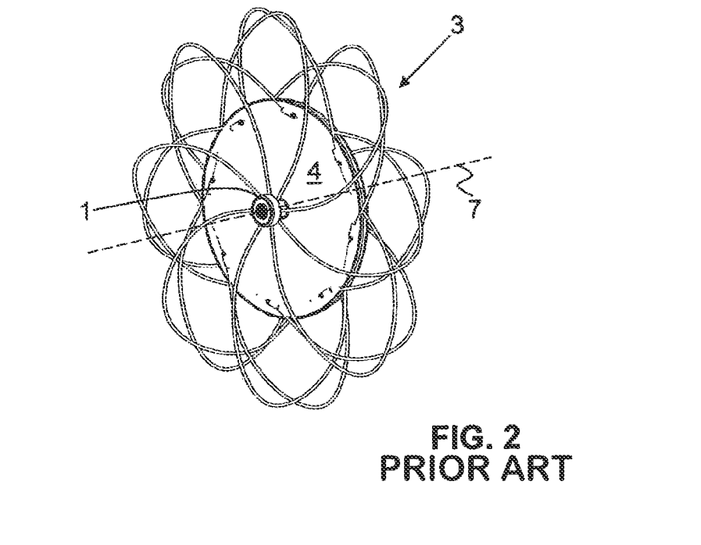
FIG. 2 shows the occluder as per FIG. 1 in the expanded manifestation.

WO 2005/074813 discloses an occluder with two expansion units and two closure bodies, which in each case rest against one side of the passage. The occluder is illustrated in FIGS. 1 and 2. The expansion units are formed by wires 3, which are held in a first coupling part 1 with a first end and in a second coupling part 2 with a second end. The wires 3 are bent by the two coupling parts 1, 2 approaching one another and form two rosette-like flat structures. The closure bodies are circular membranes 4, 5, which are penetrated by the wires 3. These membranes 4, 5 are opened by the wires 3 when the coupling parts 1, 2 are brought together. The membranes occlude the body passage from both sides. In the expanded manifestation as per FIG. 2, the coupling parts 1, 2 can be inserted into one another, and so the occluder is fixed in the manifestation.

WO 2007/115117 discloses an occluder with expansion units resting against the body passage on both sides, wherein the distance between the expansion units can be matched to the depth of the passage.

SUMMARY

It is an object of the invention to develop an improved occluder that allows adaptation to the depth of an opening to be occluded and to the width of the body wall surrounding the opening.

The occluder according to the invention for occluding an opening in a circulatory system can be converted from a compact manifestation, extending along a longitudinal axis, into an expanded manifestation, extending across the longitudinal axis. The occluder has a first expansion unit and a second expansion unit, which in each case rest against one side of the opening in the expanded manifestation. The occluder furthermore has a first coupling part and a second coupling part, which can be brought to engage into one another such that they fix the occluder in the expanded manifestation thereof. The first coupling part has a region that at least in part runs between the first and the second expansion unit in the expanded manifestation. According to the invention, the region can stretch along, i.e. in the direction of, the longitudinal axis. Advantageously, the region can also stretch counter to a restoration force, i.e. in a resilient or elastic fashion.

Because of the stretchable central region of the occluder, the distance between the two expansion units and, if present, between the two closure bodies, can be set independently. If the occluder is placed in the body opening to be occluded and brought into the expanded manifestation thereof, and if the two coupling parts are interconnected, the depth of the opening or the thickness of the body wall surrounding it determines the distance between the two expansion units. The stretchable region is stretched accordingly and so the expansion units and, if present, the closure bodies can adapt to the wall and rest against it being as planar as possible. As a result, the opening is occluded in an optimal fashion and the expansion units acting as fixing means rest against the wall in an optimal fashion.

The stretchable region may be provided on the distal and/or the proximal coupling part. Here, proximal means facing the medical practitioner and hence the entry site into the body and distal means facing away from the medical practitioner, i.e. on the patient side.

The expansion unit may form a closure unit for occluding the opening itself or it can open a separate closure body.

In a preferred exemplary embodiment, the region has a cylindrical design. The region can be a helical spring or be formed by a grid structure.

The first coupling part having the region preferably has a cylindrical hollow shaft, which can be connected in a plug-in fashion to the second coupling part, wherein the hollow shaft comprises the stretchable region. However, other types of connections between first and second coupling part are possible. By way of example, a threaded connection may be present.

The coupling parts are preferably made of metal or plastic or combinations thereof. The stretchable region is preferably made of metal.

The occluder preferably has a design as described in WO 2005/074813, mentioned at the outset, wherein the hollow shaft of the one coupling part or the one holder has a stretchable design. However, other embodiments of occluders may according to the invention likewise be provided with stretchable coupling parts.

In a preferred embodiment, the first expansion unit is attached to the first coupling part and the second expansion unit is attached to the second coupling part. The expansion units preferably have wires, the first ends of which are held in the coupling parts, wherein the wires of each expansion unit form a substantially planar structure in the expanded manifestation, the planar structure in each case rests against one side of the opening.

At least one of the two expansion units preferably has a closure body or itself forms the closure body. The closure body is preferably a membrane that is penetrated by the wires. The membrane can have a circular design or have a different shape. The membrane can preferably be opened into the expanded manifestation by means of the wires, for example by these folding over into rosette-like expansion units as a result of the action of an external force.

The two expansion units and, if present, the membranes preferably have a mirror symmetric design with respect to one another.

In one embodiment, the second coupling part has a cylindrical port, which can be inserted into the hollow shaft of the first coupling part, and the port has an encircling retention bead at the free end thereof. The first coupling part has a groove running in the interior of the hollow shaft for the purpose of connection to the retention bead. In particular, this embodiment can be used in an occluder as per WO 2005/074813, as described at the outset, or in another occluder, wherein the coupling part need not necessarily have a stretchable region.

Further exemplary embodiments are described in the dependent claims.

BRIEF DESCRIPTION OF THE DRAWINGS

Preferred embodiments of the invention are described in the following text on the basis of the drawings, which merely serve for explanation purposes and should not be construed as being restrictive. In the drawings:

FIG. 6b shows a further lateral view of the distal coupling part as per FIG. 6a;

FIG. 7b shows a further lateral view of the distal coupling part as per FIG. 7a;

DETAILED DESCRIPTION

FIGS. 1 and 2 illustrate an occluder as per the prior art. The occluder may be provided, as described below, with a coupling part according to the invention. The occluder constitutes a preferred embodiment. However, the teaching according to the invention can also be applied to other occluders.

The occluder has a distal coupling part 1 and a proximal coupling part 2. The coupling parts 1, 2 are preferably made of plastic or metal or combinations thereof. The central region described below is preferably made of metal. By way of example, the central region consists of Phynox or nitinol.

Wires 3 run between the two coupling parts 1, 2, the wires are held in the distal coupling part 1 with their first ends and in the proximal coupling part 2 with their second ends. The wires 3 and the sleeves 33 described below preferably consist of platinum iridium or nitinol or an absorbable material.

The occluder furthermore comprises two membranes 4, 5, which in each case have a central passage opening 41, 51 and peripheral passage openings 40, 50 distributed uniformly over their circumference. The membranes 4, 5 are preferably made of PET or Dacron.

The peripheral passage openings 40, 50 are penetrated by the wires 3. As a result, the individual wires 3 are subdivided into a distal wire section 30, a central wire section 31 situated between the two membranes 4, 5 and a proximal wire section 32. The wires 3 are provided with sleeves which are held on the wires in a non-displaceable fashion and define the relative position of the membranes 4, 5 to these sections 30, 31, 32. It is also possible to dispense with the sleeves or they can be replaced by similarly acting means.

The central passage openings 41, 51 have a diameter large enough to be able to be penetrated by the distal and/or proximal coupling part 1, 2. Here, the two coupling parts 1, 2 each have a flange 11, 21, the external diameter of which is preferably greater than the diameter of the passage openings 41, 51.

FIG. 1 shows how the occluder can be inserted into a body opening. The occluder has a compressed manifestation, which is not reproduced in FIG. 1. In the compressed manifestation, the occluder is drawn out and the wires 3 are almost completely stretched out. As a result, the membranes 4, 5 are crumpled up or folded together.

A catheter 6 can be used to bring the occluder to the site of the opening to be occluded. Only the distal end of this catheter 6 is reproduced in FIG. 1. The catheter 6 has a hollow catheter body 60, which is preferably formed by flexible tubing. A stiff head with a female thread has been placed onto the end of this catheter body 60. The female thread is used to connect the catheter 6 to a male thread 20 (see FIG. 8) of the proximal coupling part 2 of the occluder.

Catheter tubing 61 that passes through the proximal coupling part 2 and merges into a catheter tip runs in the catheter body 60. The catheter tubing preferably has a flexible design, wherein it can have different degrees of hardness over the length thereof and can more particularly also have a stiff region. The catheter tip is connected to the distal coupling part 1. A guide wire 62 that passes through the catheter tubing 61 eases the insertion of the compressed occluder.

The occluder is compressed and brought into the expanded manifestation thereof by applying an axial tensile force, transmitted via the catheter system, to the wires 3. The occluder is opened and expanded by pulling the distal end of the tubing 61 back toward the catheter body 60. Here, the wires 3 form a proximal and a distal expansion unit and the membranes 4, 5 form a distal and a proximal closure body. Alternatively, or in addition thereto, the occluder can also be brought into its expanded form by pushing the proximal coupling part 2 toward the distal coupling part 1 by means of the catheter body 60 and the occluder is compressed. The units and the distal and proximal closure bodies in each case come to rest against one side of the passage to be occluded. Here the wires 3 form approximately planar structures. During the bringing together they were folded to form two rosette-like or blossom-shaped forms. Thus, they twist into these forms.

Such an expanded state is illustrated in FIG. 2. The distal wire sections 31 of the wires 3 form a first expansion unit and the proximal wire sections 32 of the wires 3 form a second expansion unit. The two expansion units open the membranes 4, 5 and fix the occluder on both sides of a passage through a body wall.

Once the occluder has been placed into the passage, the tubing 61 is withdrawn further or the catheter body 60 is pushed forward further such that the two coupling parts 1, 2 engage into one another and fix the occluder in the opened position. The connections between the catheter and occluder are released and the catheter is removed.

According to the invention, at least one of the two coupling parts is equipped with a stretchable region, with at least part of this region coming to rest between the two expansion units 30, 32 in the expanded state of the occluder. In this example, the distal coupling part 1 has been provided with such a region 12.

Figure 3:
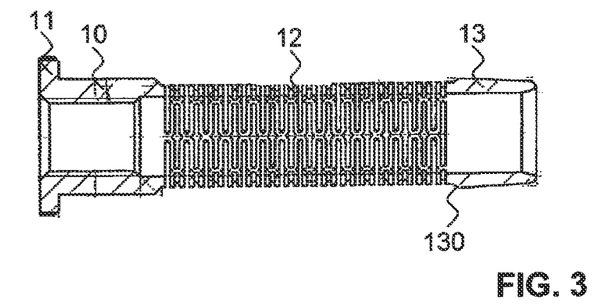
FIG. 3 shows a longitudinal section through a distal coupling part in a first embodiment.
Figure 4:
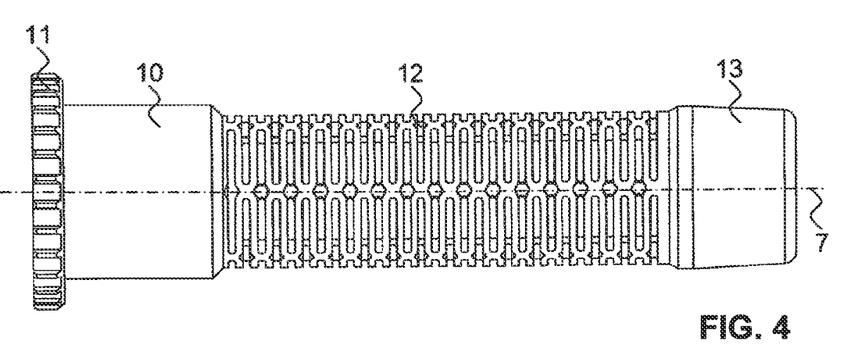
FIG. 4 shows a lateral view of the distal coupling part as per FIG. 3.
Figure 5:
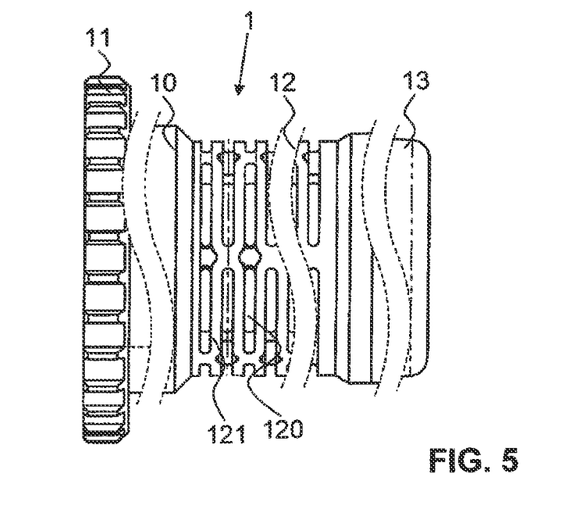
FIG. 5 shows a lateral view of the distal coupling part as per FIG. 3 in an illustration shortened along the longitudinal axis.

FIGS. 3, 4 and 5 illustrate a first exemplary embodiment of such a distal coupling part 1, which has a hollow shaft. The basic shape of the coupling part 1 is cylindrical and has a hollow design throughout with an entry opening and an exit opening. In the region of the proximal entry opening there preferably is a female thread for the connection to the catheter tubing 61.

The coupling part 1 has a distal end piece 10 with an end flange 11. The end flange 11 has a greater external diameter than the central passage opening 41 of the distal membrane 4.

In one embodiment, receptacle openings (not shown) are present in the end piece 10 or in the end flange 11, for holding and securing the ends of the wires 3. The stretchable region 12 adjoins the end piece 10. The stretchable region preferably has a constant external diameter. The external diameter is equal to or less than the diameter of the central passage opening 41 of the distal membrane 4 and, preferably, of the proximal membrane 5 as well.

FIG. 5 shows the stretchable region 12 provided with a grid structure. Webs 121 are superseded by slits 120. The grid structure can stretch along the longitudinal axis of the occluder or along the longitudinal axis of the distal coupling part 1 such that the distal coupling part 1 is elongated by the action of an external force, i.e. by the wall of the opening to be occluded. The longitudinal axes of the occluder and of the distal coupling part run congruent to one another and are provided with reference sign 7 in the Figures.

The stretchable region 12 is adjoined by an insertion port 13, which is provided with an encircling retention lug 130. The insertion port 13 can be inserted into a corresponding reception port of the associated proximal coupling part 2 and can be fixed in a corresponding inner groove of the proximal coupling part 2 by means of the retention lug 130.

Figure 6A:
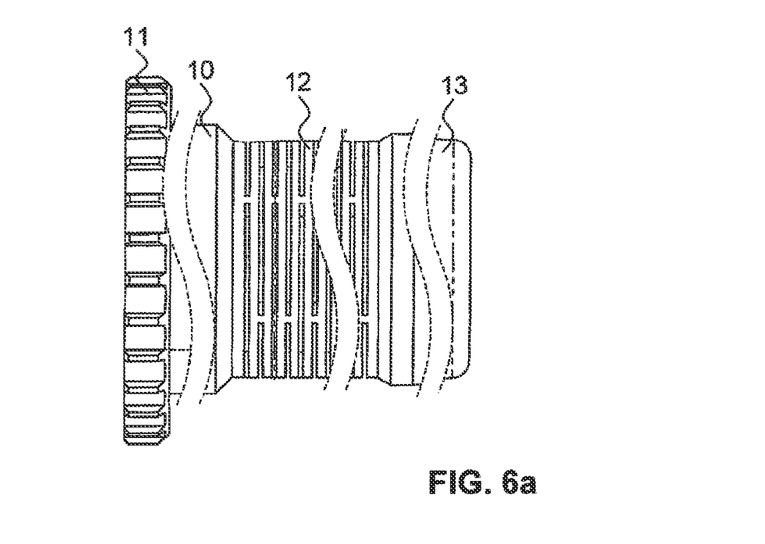
FIG. 6a shows a lateral view of a distal coupling part as per a second embodiment in an illustration shortened along the longitudinal axis.
Figure 6B:
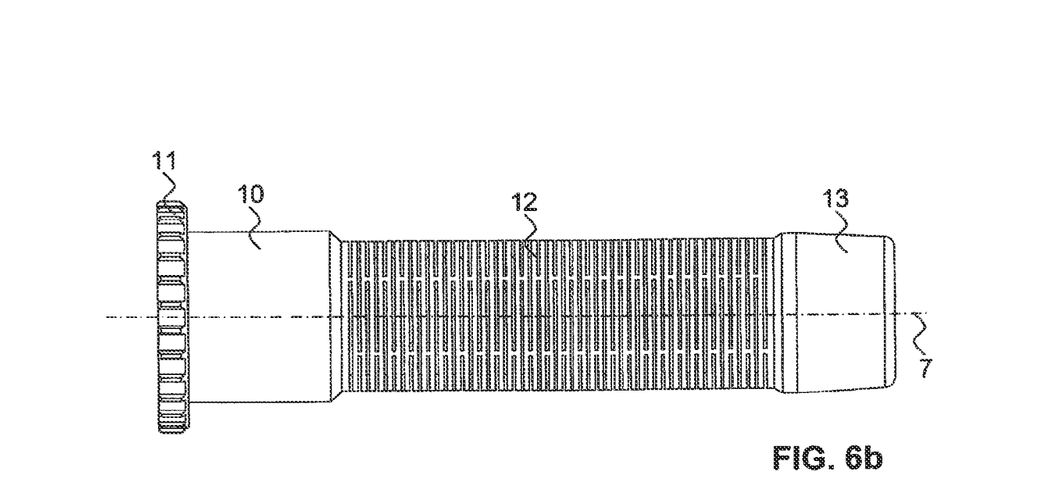

FIGS. 6a and 6b illustrate a second exemplary embodiment. The distal coupling part has substantially the same design as in the example described above. However, the grid structure of the stretchable region 12 has a different form. The webs and slits have a narrower design than in the first example.

Figure 7A:
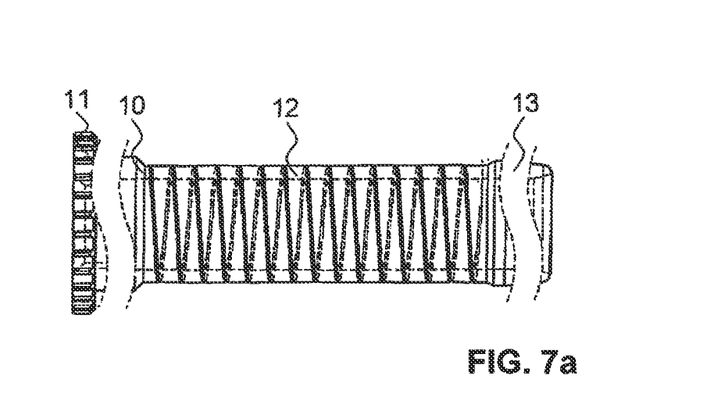
FIG. 7a shows a lateral view of a distal coupling part as per a third embodiment in an illustration shortened along the longitudinal axis.
Figure 7B:
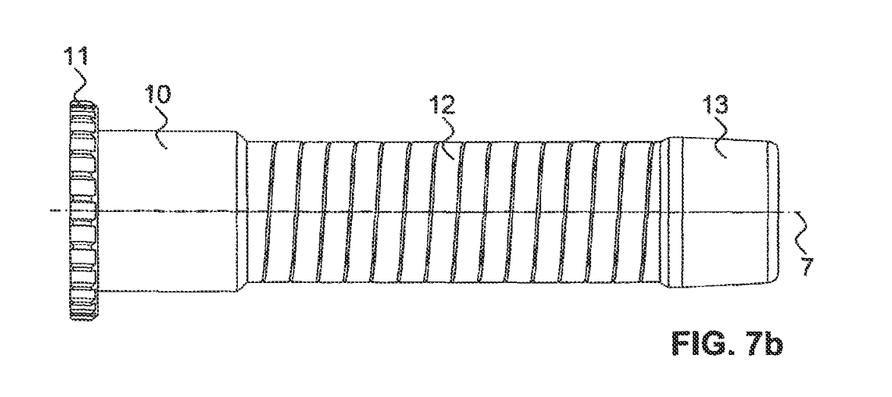

In the third embodiment as per FIGS. 7a and 7b, the stretchable region 12 is embodied as a helical spring or the stretchable region 12 is provided with a helically encircling slit.

Figure 8:
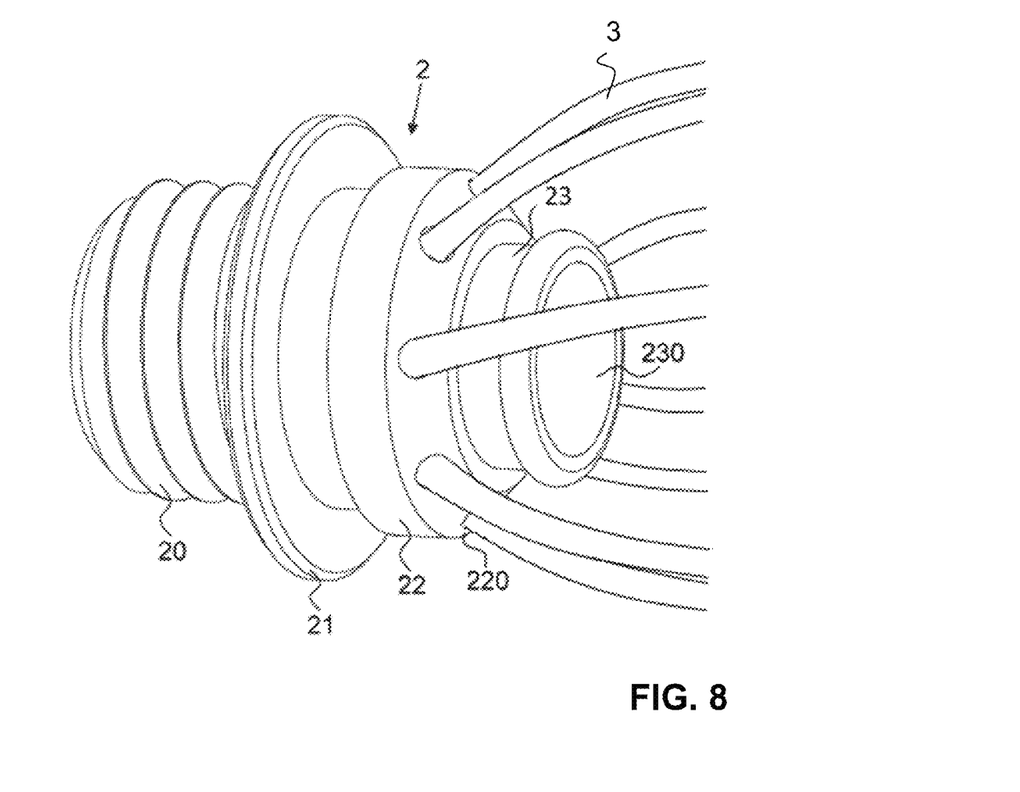
FIG. 8 shows a perspective illustration of a proximal coupling part as per a fourth embodiment.
Figure 9:
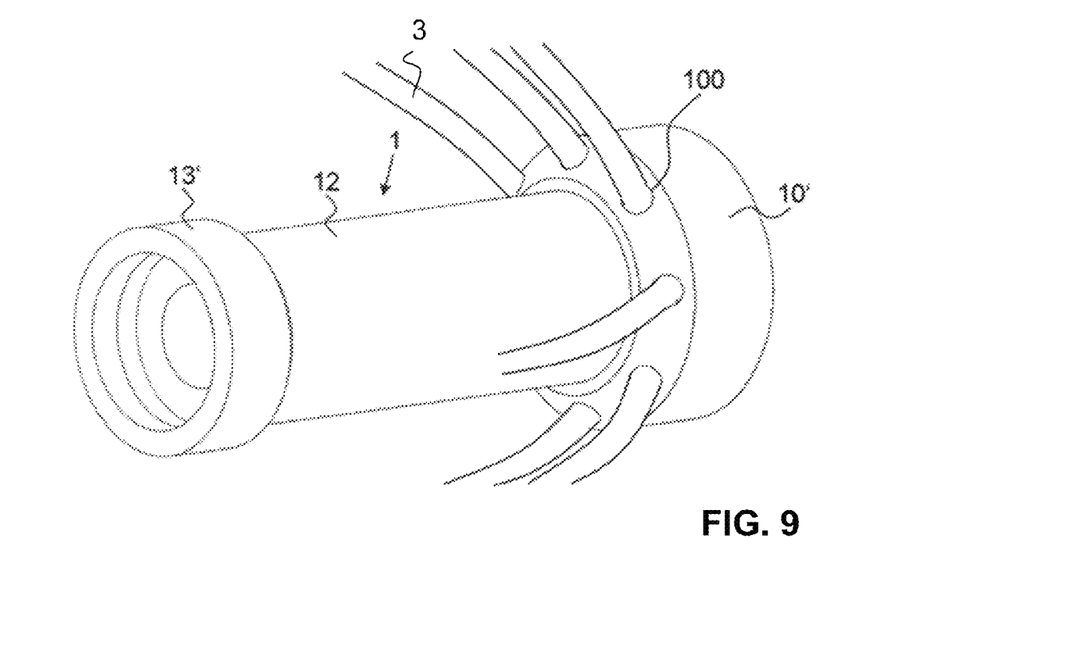
FIG. 9 shows a perspective illustration of a distal coupling part, which is associated with the proximal coupling part as per FIG. 8.
Figure 10:
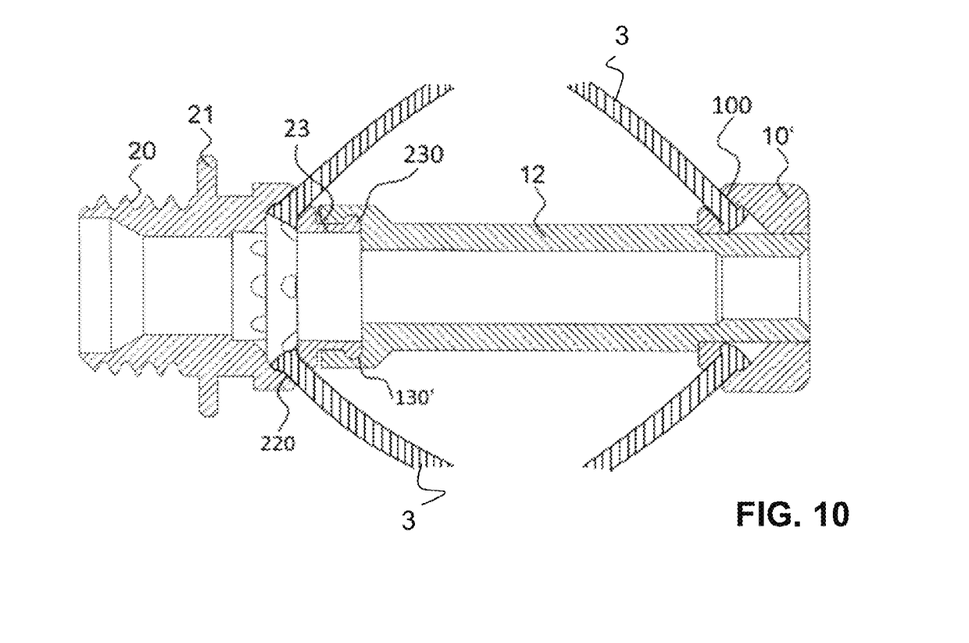
FIG. 10 shows a longitudinal section through the coupling parts as per FIGS. 8 and 9, which engage into one another.

In the embodiment showing FIGS. 8 to 10, the proximal coupling part 2 is inserted into the distal coupling part 1. The proximal coupling part 2 in FIG. 8 has a threaded port 20 with a male thread for the connection to the catheter body 60. The port 20 is adjoined by the flange 21, which has a greater external diameter than the central passage opening 51 of the proximal membrane 5. The flange 21 is adjoined by the receptacle body 22 with the receptacle openings 220, in which the ends of the wires 3 are held. An insertion port 23 with an encircling retention bead 230 forms the distal end of this coupling part 2.

The counterpart thereof is illustrated in FIG. 9. Here the distal coupling part 1 has a distal end piece 10', which has receptacle openings 100 and is embodied as a flange. The proximal end of this coupling part 1 is formed by a receptacle port 13', into which the insertion port 23 can be inserted. In the receptacle port 13' there is a groove 130' into which the retention bead 230 engages, as shown in FIG. 10. Alternatively, the coupling can also be brought about in the same fashion as the coupling as per the embodiments illustrated in FIGS. 3, 4 and 6b.

The embodiment in FIGS. 8 to 10 also has a stretchable region 12, which can have the same design as in the examples described above.

Moreover, FIG. 10 the distal coupling part 1 having a two-part design. The base body, which comprises the stretchable region 12, is preferably made of metal or plastic. At one end, the base body 12 is surrounded by a sleeve 10', which forms the end piece of the distal coupling part 1. Receptacle openings 100 for holding the wires 3 are present in this end piece 10'. The sleeve 10' is preferably pushed over the distal end of the stretchable region 12 and is held there in an interlocking fashion. At the distal end, the stretchable region 12 can have a radially outwardly protruding flange, which can snap into a corresponding, internal encircling groove or ledge in the sleeve 10' (not shown). Preferably, the distal end piece 10' and the proximal coupling part 2 are made of plastic. The two-part design and the specified material selection can also be applied to the other exemplary embodiments described here.

Figure 11:
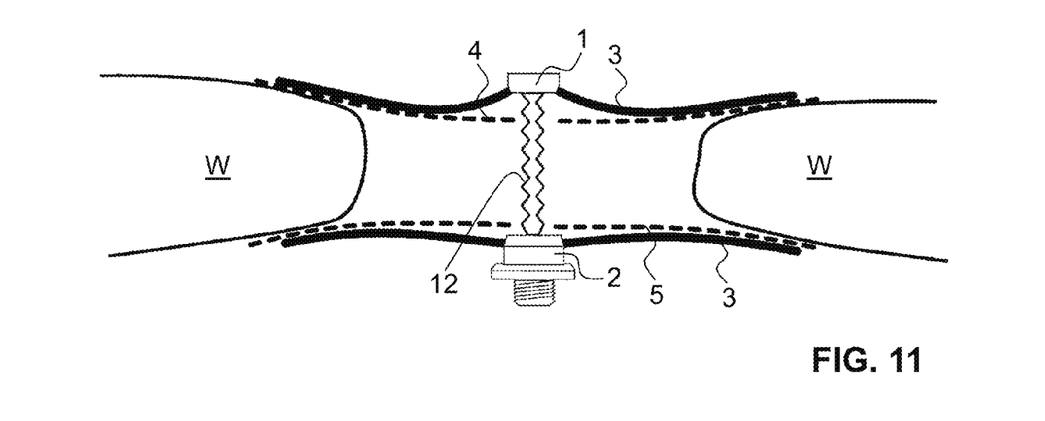
FIG. 11 shows a schematic illustration of an occluder placed into an opening in a first application and FIG. 12 shows a schematic illustration of an occluder placed into an opening in a second application.
Figure 12:
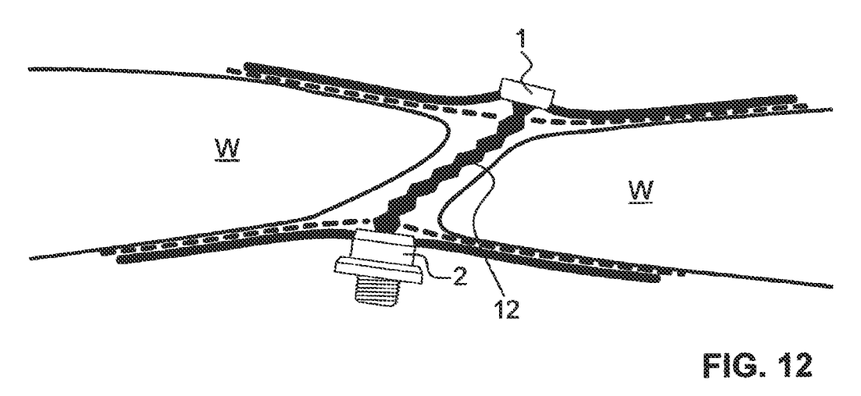

In FIGS. 11 and 12, the occluder is placed into a body opening to be occluded. The rosette-like bent wires 3 and the membranes 4, 5 rest against both sides of the body wall W. The coupling parts 1, 2 have been brought to engage with one another; preferably they are inserted into one another. It is possible to identify how the stretchable region 12 situated between the expansion units 3 and between the membranes 4, 5 matches the external conditions and expands such that the expansion units 3 and the membranes 4, 5 can rest being as planar as possible against both sides of the wall W.

The occluder according to the invention thus allows independent setting of the distance between two expansion and/or closure units according to the stipulation of the structural conditions at the location of the opening to be occluded.

The invention claimed is:

1. An occluder for occluding an opening in a circulatory system, wherein the occluder can be converted from a compact manifestation, extending along a longitudinal axis, into an expanded manifestation, wherein the occluder has a first expansion unit and a second expansion unit, which are configured to rest against opposite sides of the opening in the expanded manifestation, and wherein the occluder furthermore has a first coupling part and a second coupling part, wherein the first coupling part and the second coupling part are configured to be brought together at a site of the opening to be occluded, wherein the first coupling part forms a distal end of the occluder and the second coupling part forms a proximal end of the occluder, wherein the first coupling part has a region that at least in part runs between the first and the second expansion unit in the expanded manifestation, wherein the region is stretchable along the longitudinal axis, wherein the first expansion unit is attached to the first coupling part and the second expansion unit is attached to the second coupling part, wherein the first expansion unit and the second expansion unit are formed by wires running between the first and the second coupling parts, each of said wires comprising a first end and a second end, the first end being held in or attached to the first coupling part and the second end being held in or attached to the second coupling part, and wherein the first expansion unit and the second expansion unit are brought from the compact manifestation into the expanded manifestation by bringing the first coupling part and the second coupling part together, and wherein a portion of the first coupling part is insertable into a portion of the second coupling part or wherein a portion of the second coupling part is insertable into a portion of the first coupling part to fix the occluder in the expanded manifestation thereof.

2. The occluder as claimed in claim 1, wherein the region has a resilient design.

3. The occluder as claimed in claim 1, wherein the region has a cylindrical design.

4. The occluder as claimed in claim 1, wherein the region is formed by a helical spring.

5. The occluder as claimed in claim 1, wherein the region is formed by a grid structure.

6. The occluder as claimed in claim 1, wherein the first coupling part has a cylindrical hollow shaft, which can be connected in a plug-in fashion to the second coupling part, wherein the hollow shaft comprises the stretchable region.

7. The occluder as claimed in claim 6, wherein the second coupling part has a cylindrical port, which can be inserted into the hollow shaft of the first coupling part, wherein the port has an encircling retention bead at a free end, and wherein the first coupling part has a groove running in the interior of the hollow shaft for connection to the retention bead.

8. The occluder as claimed in claim 1, wherein the stretchable region is made of metal.

9. The occluder as claimed in claim 1, wherein the first end of each wire is held in the first coupling part and the second end of each wire is held in the second coupling part, wherein the wires form a substantially planar structure being the first expansion unit in the expanded manifestation and the wires form a second substantially planar structure being the second expansion unit in the expanded manifestation, and wherein the first substantially planar structure is configured to rest against a first side of the opening and the second substantially planar structure is configured to rest against a second side of the opening, the second side being opposite to the first side.

10. The occluder as claimed in claim 9, wherein at least one of the two expansion units has a closure body, wherein the closure body is a membrane that is penetrated by the wires.

11. The occluder as claimed in claim 1, wherein at least one of the two expansion units has a closure body.

12. The occluder as claimed in claim 11, wherein the closure body can be opened into the expanded manifestation by means of the wires of the associated expansion unit.

13. The occluder as claimed in claim 1, wherein the two expansion units have a mirror symmetric design with respect to one another.

14. The occluder as claimed in claim 1, wherein the region is stretchable along the longitudinal axis with the portion of the first coupling part being inserted into the portion of the second coupling part or with the portion of the second coupling part being inserted into the portion of the first coupling part.

* * * * *